US00PP32798P2

(12) United States Plant Patent
Zary

(10) Patent No.: US PP32,798 P2
(45) Date of Patent: Feb. 9, 2021

(54) ROSE PLANT NAMED 'ZARSUNORNU'

(50) Latin Name: *Rosa hybrida*
Varietal Denomination: ZARsunornu

(71) Applicant: American Daylily and Perennials, Inc., Grain Valley, MO (US)

(72) Inventor: Keith W. Zary, Missoula, MT (US)

(73) Assignee: American Daylily and Perennials, Inc., Grain Valley, MO (US)

( * ) Notice: Subject to any disclaimer, the term of this patent is extended or adjusted under 35 U.S.C. 154(b) by 0 days.

(21) Appl. No.: 16/602,842

(22) Filed: Dec. 10, 2019

(51) Int. Cl.
*A01H 5/02* (2018.01)
*A01H 6/74* (2018.01)

(52) U.S. Cl.
USPC ..... Plt./104
CPC ..... *A01H 6/749* (2018.05)

(58) Field of Classification Search
USPC ..... Plt./104
CPC ..... A01H 5/0222
See application file for complete search history.

(56) References Cited

PUBLICATIONS https://www.floraldaily.com/article/9063284/new-mandevilla-is-naturally-resistant-to-mites/; Jan. 18, 2019; 3 pages.*
http://suntoryflowers.com/wp-content/uploads/2020/03/2021-SuntoryCatalog-FINAL.pdf; May 19, 2020; 2 pages.*

* cited by examiner

*Primary Examiner* — Kent L Bell
(74) *Attorney, Agent, or Firm* — Weatherly IP Solutions, LLC; Barbara Campbell

(57) ABSTRACT

A new and distinct variety of shrub rose having an upright, compact, and well-branched habit, and yellow flowers, is disclosed.

1 Drawing Sheet

Genus and species: *Rosa hybrida.*
Denomination: 'ZARsunornu'.

BACKGROUND

'ZARsunornu' is a new and distinct variety of shrub rose. 'ZARsunornu' was observed as a sport branch, naturally-occurring mutation on the parent 'ZARsunorgdlt' (U.S. Plant Pat. No. 25,825) in May 2017 in Sarasota, Fla. The sport was propagated by cuttings under midst for several generations to test for stability and performance.

Other subsequent asexual propagations were conducted in controlled environments in Tipp City, Ohio and demonstrate that 'ZARsunornu' reproduces true to type in successive generations of asexual reproduction via softwood cuttings, budding, and grafting.

SUMMARY

The following are the most outstanding and distinguishing characteristics of this new variety when grown under normal horticultural practices in Sarasota, Fla. and Tipp City, Ohio.

1. A shrub rose having an upright, compact, and well-branched habit; and
2. Yellow flowers.

DESCRIPTION OF THE PHOTOGRAPH

This rose plant is illustrated by the accompanying photographs which shows the individual parts of the plant and the whole plant habit. The photographs were taken in Tipp City, Ohio in May 2019 on 18-month-old plants. The colors shown are as true as can be reasonably obtained by conventional photographic procedures. The colors shown are as true as can be reasonably obtained by conventional photographic procedures.

Figure 1:
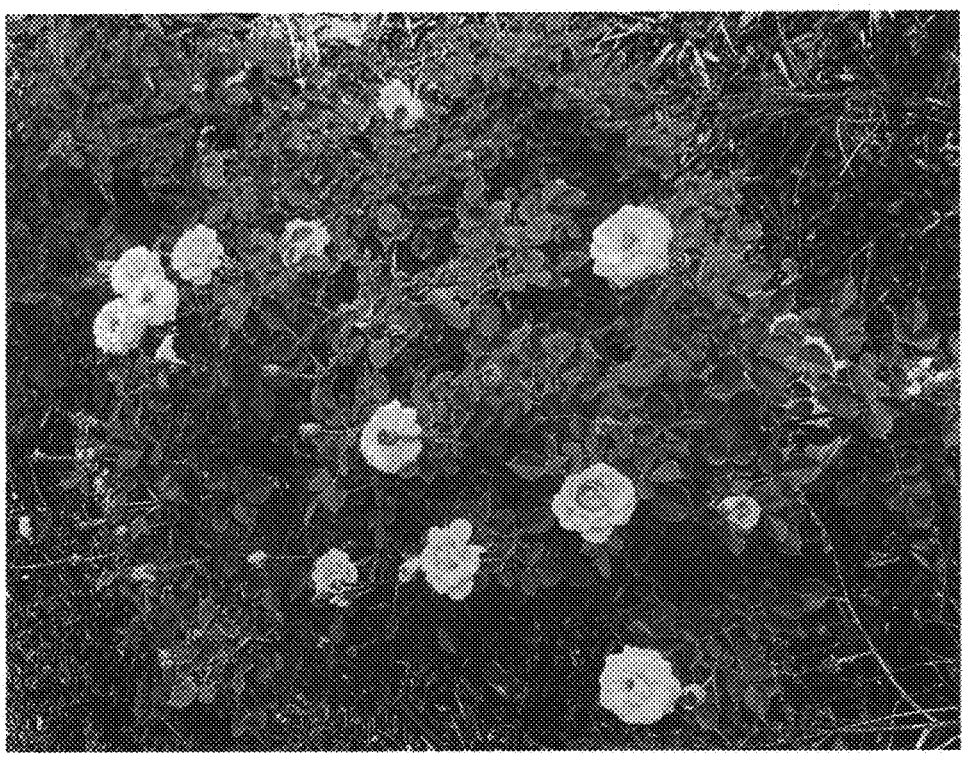

FIG. 1 shows a whole plant photograph of 'ZARsunornu'.

Figure 2:
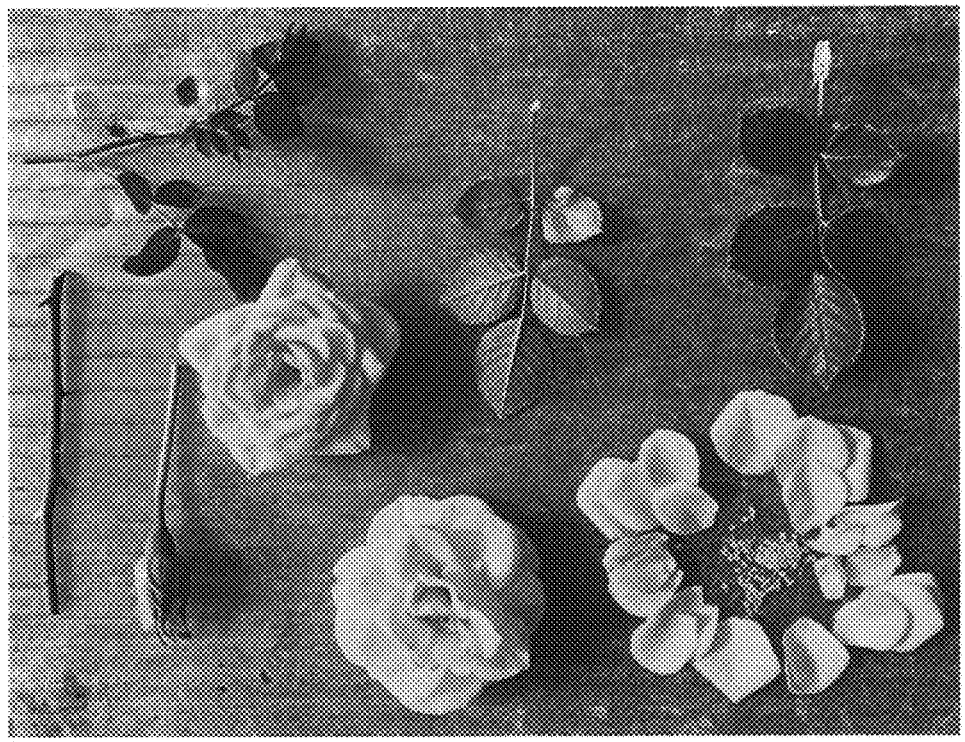

FIG. 2 shows from top to bottom, starting at the top (first) row from left to right, a stem with mature and immature leaves, the lower surface of a compound leaf, and the upper surface of a compound leaf; bottom row, from left to right, a part of an individual stem showing thorns, a bud attached to part of a stem, the upper surface of a flower in mid-bloom, the upper surface of a flower in mid bloom, and a flower showing the individual petals and stamens pulled out.

DETAILED DESCRIPTION

The following detailed descriptions set for the distinctive characteristics of 'ZARsunornu'. The data which define these characteristics were collected from asexual reproductions carried outdoors in Tipp City, Ohio and Sarasota, Fla. from June 2017 to May 2019 on plants that were two-years-old. The phenotype of this new variety will vary somewhat with variation in environmental, climatic, and cultural conditions as it has not been tested in other environments. Color references are to The R.H.S. Colour Chart of The Royal Horticultural Society of London (R.H.S.) 2001.

Classification:

*Family.*—Rosaceae.
*Species.*—*Rosa hybrida.*
*Common name.*—Shrub rose.
*Variety.*—'ZARsunornu'.

Parentage:

*Female parent*.—'ZARsunorgdlt' (U.S. Plant Pat. No. 25,825).

Plant:

*Growth habit*.—Upright, compact, well branched.

*Height*.—30.0 cm.

*Spread*.—24.0 cm.

*Life cycle*.—Perennial.

*Propagation type*.—Softwood cuttings.

*Time to produce a rooted cutting*.—18 to 21 days under mist at 25 to 27 degrees Celsius.

*Root description*.—Fibrous, dense.

*Time to bloom from propagation*.—8 to 10 weeks.

*Lastingness of inflorescence on the plant*.—5 to 6 days.

*USDA hardiness zones*.—Hardy from zone 5 to zone 11.

Stems:

*Color, young stems*.—RHS 146B.

*Color, mature stems*.—RHS 199B.

*Surface texture, young stems*.—Smooth with occasional prickle (thorn).

*Surface texture, mature stems*.—Smooth.

*Stem shape in cross-section*.—Round.

*Diameter*.—2.0 mm.

*Length*.—10 cm to 12 cm.

*Anthocyanin*.—Absent.

*Internode length*.—1.5 cm.

*Thorns*.—Density (quantity per unit area): 9 to 10 per 8 cm of stem. Shape: Straight, needle shaped. Color: RHS 199B on mature wood; RHS 193C on immature wood. Length: 5.0 mm. Width (at the base): 1.0 mm.

Foliage:

*Arrangement*.—Odd pinnate.

*Quantity of leaflets per leaf*.—5.

*Leaf length*.—8.0 cm.

*Leaf width*.—5.0 cm.

*Terminal leaflet*.—Length: 3.0 cm. Width: 2.0 cm. Shape: Elliptic. Apex: Acuminate. Base: Rounded. Margin: Serrate. Color, immature leaf: Upper surface: RHS 146B. Lower surface: RHS 147C with some RHS 178D on leaf edges. Color, mature leaf: Upper surface: RHS 137A. Lower surface: RHS 138B. Texture: Upper surface: Glossy, smooth, coriaceous. Lower surface: Smooth.

*Lateral leaflet*.—Length: 2.0 cm. Width: 1.5 cm. Shape: Elliptic. Apex: Acute. Base: Oblique. Margin: Simply serrate. Color, immature leaf: Upper surface: RHS 146B. Lower surface: RHS 147C with RHS 178D on leaf edges. Color, mature leaf: Upper surface: RHS 137A. Lower surface: RHS 138B. Texture: Upper surface: Glossy, smooth and coriaceous. Lower surface: Smooth.

*Leaflet venation pattern*.—Reticulate.

*Leaflet venation color*.—Upper surface: RHS 137A. Lower surface: RHS N138B.

*Petioles, leaves*.—Length: 5.0 cm. Diameter: 1.0 mm. Color: RHS 146B. Texture: Rough with prickles and with glands. Thorns: There are about 8 thorns per 10 cm of stem; color is RHS 199B for mature thorns and RHS 193C for immature thorns; length is 0.5 cm.

*Petioles, leaflets*.—Length: 1.0 mm. Diameter: 1.0 mm. Color: RHS N138B. Texture: Smooth. Thorns: There are no prickles (thorns) on the leaflet petiole. There are prickles on the leaf petiole. The leaflet petiole is only 1.0 mm long and is quite smooth.

*Stipules*.—Arrangement and appearance: Parallel, auricles facing slightly downward, adnate. Length: 10.0 mm. Width: 3.0 mm. Shape: Adnate, parallel, auricles facing slightly downward. Apex: Truncate with auricles. Base: Truncate. Margin: Rough with glands. Color, immature leaf: Upper surface: RHS 146D; at the base there is a small area of RHS 178D. Lower surface: RHS 146D; at the base a small area of RHS 178D. Color, mature leaf: Upper surface: RHS 146B. Lower surface: RHS 146B. Texture: Upper surface: Smooth, edged in glands. Lower surface: Smooth, edged in glands.

Flowers or inflorescence:

*Appearance and arrangement*.—Borne singly and in small clusters of 3 to 5 of pyramidal shape.

*Flowering season*.—From 6 weeks after spring frost to fall frost; in Ohio, this is from late March to mid-October.

*Fragrance*.—None observed.

*Diameter*.—4.5 cm when fully open.

*Depth or height*.—1.5 cm when fully open.

*Lastingness of flowers on the plant*.—5 to 6 days.

*Buds*.—Length: 2.0 cm when bud is starting to open. Width: 1.0 cm when bud is starting to open. Surface texture: Smooth. Shape: Pointed ovoid. Margin: Entire. Color: RHS 13A.

*Petals*.—Quantity per flower: 30 to 35. Length: 2.0 cm. Width: 2.0 cm. Shape: Orbicular. Apex: Rounded. Base: Rounded. Margin: Entire. Color, when opening: Upper surface: RHS 13A. Lower surface: RHS 13A. Color, when fully open: Upper surface: RHS 13A fading to RHS 13C after 5 days. Lower surface: RHS 13A fading to RHS 13C after 5 days. Surface texture: Upper surface: Smooth. Lower surface: Smooth.

*Sepals*.—Quantity per flower: 5. Length: 1.5 cm. Width: 0.5 cm. Shape: Lanceolate. Apex: Acute to aristate. Base: Truncate. Margin: Either hoary or hoary and pinnatified. Color, when opening: Upper surface: RHS 191C. Lower surface: RHS 146B overlaid with RHS 183D in sun exposed areas. Color, when fully open: Upper surface: RHS 191C. Lower surface: RHS 146B. Surface texture: Upper surface: Glandular. Lower surface: Hoary.

*Peduncles*.—Length: 4.5 cm. Diameter: 0.3 cm. Texture: Smooth. Color: RHS 137C overlaid with RHS 178A when exposed to direct sun.

Reproductive organs:

*Stamens*.—Quantity per flower: 35 to 40. Anther color: RHS 16C. Anther shape: Oblong. Filament length: 0.4 cm. Filament color: RHS 7D. Pollen amount: Sparse. Pollen color: RHS 163A.

*Pistils*.—Quantity per flower: 30. Pistil length: 0.3 cm. Stigma shape: Orbicular. Stigma color: RHS 156D. Style length: 0.2 cm. Style color: RHS 180D. Receptacle: Height: 0.5 cm. Diameter: 0.7 cm. Color: RHS 146B. Texture: Smooth.

*Fruit and seed set*.—None observed.

Disease resistance: Resistant to the common rose diseases of Powdery Mildew, rust and black spot; pest resistance and susceptibility unknown.

COMPARISON WITH PARENTAL AND COMMERCIAL LINES

'ZARsunornu' can be compared with the mutation parent 'ZARsunorgdlt' (U.S. Plant Pat. No. 25,825) as shown in Table 1.

TABLE 1

| comparison with parental line | | |
|---|---|---|
| Characteristic or trait | 'ZARsunornu' | Female Parent 'ZARsunorgdlt' |
| Flower color | RHS 13A | RHS 29C with RHS 13C at petal base |

When 'ZARsunornu' is compared to the commercial comparison rose variety 'WEkcofbunk' (U.S. Plant Pat. No. 23,324), the following differences are noted in Table 2.

TABLE 2

| comparison with commercial line | | |
|---|---|---|
| Characteristic | 'ZARsunornu' | 'WEkcofbunk' |
| Flower color | 13C | 25A |

I claim:

1. A new and distinct variety of rose plant designated 'ZARsunornu' as illustrated and described herein.

* * * * *